United States Patent [19]

Luong et al.

[11] Patent Number: 4,973,554
[45] Date of Patent: Nov. 27, 1990

[54] AFFINITY PROCESS FOR TRYPSIN PURIFICATION AND STABILIZATION

[75] Inventors: John H. Luong, Mount-Royal; Keith B. Male, Verdun; An-Lac Nguyen, Dollard des Ormeaux, all of Canada

[73] Assignee: National Research Council of Canada, Ottawa, Canada

[21] Appl. No.: 160,698

[22] Filed: Feb. 26, 1988

[30] Foreign Application Priority Data

May 29, 1987 [CA] Canada ................................. 538411

[51] Int. Cl.$^5$ .............................................. C12N 9/76
[52] U.S. Cl. .................................... 435/213; 530/413
[58] Field of Search ......................... 435/213; 530/413

[56] References Cited

U.S. PATENT DOCUMENTS 4,350,760  9/1982  Nicolas ............................ 435/26 X

OTHER PUBLICATIONS

Annals of N.Y. Acad. of Sci. 369,257–263 (1981), Schneider.
J. of Membrane Science, 9, 337–342 (1981), Adamski-Medda.
Annals of N.Y. Acad. of Sci. 413, 307–309 (1983), Mattiasson.
Biotechnology Letters, vol. 8, No. 3, 163–168 (1986), Choe.

Primary Examiner—Howard E. Schain
Attorney, Agent, or Firm—Alan A. Thomson

[57] ABSTRACT

A water soluble ligand bound polymer has been synthesized and used for purification and stabilization of trypsin, an easily autodigestible enzyme. The affinity polymer was formed by copolymerizing N-acryloyl-m-amino-benzamidine, and acrylamide in the absence of oxygen. Bound trypsin could be easily eluted by either arginine or benzamidine. At low temperature (<5° C.), the polymer solution was very stable and retained its high capacity for trypsin binding after 6 months of storage. Trypsin can also be stored in this system for extended periods. Combining the principles of affinity chromatography and ultrafiltration, a process has been developed, using this polymer, for purification of trypsin. The purification process also features provisions for the recirculation of the eluant as well as the macroligand.

24 Claims, 3 Drawing Sheets

AFFINITY PROCESS FOR TRYPSIN PURIFICATION AND STABILIZATION

BACKGROUND AND PRIOR ART

This invention relates to the use of a water soluble reusable macroligand for the purpose of purification and stabilization of trypsin. This novel composition provides improved trypsin purification results.

Besides insulin, beef pancreas contains many other valuable compounds such as trypsin, chymotrypsin, carboxypeptidase, elastase, lipase, etc. Pancreas is rather expensive and the size of the slaughter limits the total pancreas supply. Therefore, one should make the best possible use of this tissue by recovering most of the above-mentioned biological compounds.

The recovery of trypsin from beef pancreas is of industrial interest since this enzyme has been widely used for medical purposes; beer haze removal; and meat tenderization. It is, however, quite difficult to isolate and purify trypsin by conventional purification procedures, such as precipitation by salts or solvents, since pancreas contains two very similar enzymes (in terms of molecular weight, isoelectric pH, etc.): trypsin and chymotrypsin. The difference between trypsin and chymotrypsin can only be distinguished by the catalytic reaction. Trypsin catalyzes the hydrolysis of only the peptide bond in which the carboxyl group is contributed by either a lysine or an arginine residue, regardless of the length or amino acid sequence of the chain. Chymotrypsin, on the other hand, attacks only the peptide bonds in which the carboxyl group is contributed by one of phenylalanine, tryptophan, and tyrosine.

For the last decade, several affinity chromatographic methods based on proteinaceous inhibitors have been developed for trypsin purification (G. Feinstein, Biochim. Biophys. Acta, 214, 244, 1970; G. Feinstein, Fed. Eur. Biochem. Soc. Lett., 7, 353, 1970; N. Robinson, R. Tye, H. Neurath and K. Walsh, Biochemistry, 10, 2743, 1971). The system is composed of a stationary insoluble matrix, such as derivatives of cellulose, polyacrylamide, polystyrene, beaded agarose, etc., to which a ligand molecule (trypsin inhibitors) is covalently bound. Such a procedure, however, is costly, laborious and time consuming since the ligands are expensive, difficult to prepare, susceptible to degradation and only have a limited operating life. Furthermore, this system uses a packed column that can plug and foul and, therefore, cannot be used on whole broths as can other techniques, e.g. two-phase extraction (G. Johanson, J. of Biotech., 3, 11, 1985). As a result, conventional affinity chromatography can only be used for processing a fairly clear liquid solution containing proteins and/or enzymes.

Ultrafiltration, another widely used technique, can be utilized to separate solutes from one another or solutes from solvents. Besides its ease of scale-up, ultrafiltration possesses a high productivity and it can be operated as batch or continuous systems. There are, however, disadvantages to ultrafiltration because of its low resolution. In practice, a resolution of ten-fold difference in molecular weight is about the best that can be expected.

There is a recent breakthrough in the isolation and purification of biomolecules such as proteins, enzymes and hormones. The technique has been defined as affinity-ultrafiltration where a specific ligand is chemically bound to a macromolecular water soluble polymer (B. Mattiason and M. Ramstorp, Annals of N.Y. Academy of Sciences, 413, 307, 1983). By using a suitable ultrafiltration membrane the desired product will be retained since it formed a complex with the ligandbound macromolecules. The product is then eluted from the polymer under suitable conditions. In this example, concanavalin-A was purified using heat-killed cells of *Saccharomyces cerevisiae* as the affinity absorbent and D-glucose as the eluant. Further, Adamski-Medda et al (J. Membrane Science, 9, 337, 1981) utilized dextran-p-aminobenzamidine as a macroligand to separate trypsin and chymotrypsin. The results indicated a low degree of binding specificity. In fact, in the presence of the macroligand the filtrate contained 65% of chymotrypsin and 24% of trypsin. Choe et al (Biotech. Letters, 3, 163, 1986) also attempted to separate trypsin from chymotrypsin using soybean trypsin inhibitor as well as p-aminobenzamidine attached to dextran. The results were not very encouraging either, since only 55% of trypsin input was recovered at a purity of 81%. It was almost apparent through the two proceeding studies that dextran exhibited some non-specific affinity toward chymotrypsin as well as trypsin.

The process described in this application is an improved method over the prior art for it provides a higher enzyme to ligand binding ratio, less fouling to the membrane occurs and the binding is more specific. For example, in a batchwise procedure, the ligand described in this application could purify trypsin from a trypsin-chymotrypsin mixture with 90% yield and a purity of 98%.

U.S. Pat. No. 4,350,760 (J-C. Nicolas et al, Sept. 21, 1982) teaches a method for selective separation of at least one protein having an affinity for a ligand, from other substances, some of them having the same affinity for said ligand but also having a high molecular weight, higher than that of the protein to be isolated. The method consists of filtering the solution containing the proteins on a gel excluding the substances with the higher molecular weight. The gel is coupled with a ligand having affinity for the substance to be purified. The present application differs from the patented process in that the substances to be separated have the same molecular weight but have different affinity to the ligand.

Schneider et al (Annals of N.Y. Academy of Sciences, 369, 257, 1981) developed an affinity precipitation technique for the isolation and purification of trypsin from bovine pancreas. In this reference, a water soluble polymer (polyacrylamide) bearing a ligand group (benzamidine) and a precipitation group (benzoic acid) is described which permits a quantitative precipitation of the affinity polymer. In this technique, the polymer is added directly to a crude extract under conditions favoring the binding of the desired protein. The polymer is then precipitated and the supernatant is removed. The protein of interest is then eluted from the polymer under suitable conditions and the polymer can be recycled. Obviously, a procedure using acidic pH for the precipitation of the polymer and for the elution of the bound protein cannot be used for all enzymes, as many are unstable in acidic media. In addition, this method can only be used in a batchwise procedure, whereas the present application also teaches a method for the continuous purification of trypsin.

SUMMARY OF THE INVENTION

The object of this invention is to provide an improved method of trypsin purification using an affinity-ultrafiltration process.

According to the present invention, there is provided a method for purifying trypsin comprising: (a) incubating the enzyme containing mixture with an affinity polymer, formed by copolymerizing N-acryloyl-aminobenzamidine and acrylamide to an average molecular weight of at least about 100,000; (b) ultrafiltering the solution of (a) to remove all enzymes not bound to the affinity polymer, and retaining the enzyme-affinity polymer complex; (c) removing the purified trypsin, bound to the affinity polymer, by eluting with a selected eluting solution and recovering the polymer; and (d) ultrafiltering the resulting solution from (c) to separate the purified trypsin and the eluant.

In one embodiment of the present invention, the affinity polymer, is formed by copolymerizing N-acryloyl-m-aminobenzamidine and acrylamide, wherein the ratio of the acrylamide to monomer is 10:1–2:1, preferably 5:1, and the concentration of the acrylamide is 0.3–3%, preferably 0.75%.

In another embodiment of the present invention, the eluting solution is selected from the group consisting of benzamidine, L-arginine and m-aminobenzamidine, preferably 500 mM L-arginine.

Further, according to the present invention, there is provided a continuous affinity-ultrafiltration process for purifying trypsin comprising: (a) contacting an enzyme solution, containing trypsin, with the affinity polymer, formed by copolymerizing N-acryloyl-aminobenzamidine and acrylamide, to an average molecular weight of at least about 100,000; (b) ultrafiltering the solution of (a) to remove all enzymes not bound to the affinity polymer and to recover the affinity polymer-trypsin complex; (c) adding fresh polymer and enzyme solution to the first container while withdrawing the affinity-polymer-trypsin complex; (d) adding a selected eluting solution to the withdrawn complex to dissociate the trypsin from the affinity polymer; (e) ultrafiltering the solution from step (d) to recover the dissociated trypsin and eluant; and (f) ultrafiltering the residual solution to recover the purified trypsin.

In some embodiments of the present invention, the ultrafiltration units of steps (b) and (e) are equipped with filters with a molecular weight cut-off of 100,000 and the ultrafiltration unit of step (f) is equipped with filters with a molecular weight cut-off of 10,000.

In other embodiments of the present invention the eluant solution of step (d) is 1M L-arginine or 50 mM benzamidine.

In a preferred embodiment of the present invention, the affinity polymer from step (d) is regenerated for re-use in step (a) and the eluant recovered from step (f) is recirculated to step (d).

Further, according to the present invention, there is provided a method of stabilizing and storing trypsin comprising binding trypsin to the affinity polymer and storing the trypsin-polymer complex. After storage, the trypsin is recovered by elution with an eluting solution and ultrafiltration.

DESCRIPTION OF THE DRAWINGS

In the accompanying drawings which illustrate, by way of example, embodiments of the present invention.

DETAILED DESCRIPTION

This invention relates to the use of a water soluble re-usable macroligand for the purpose of purification and stabilization of trypsin.

The water soluble macroligand was formed by copolymerizing N-acryloyl-aminobenzamidine and acrylamide in the absence of oxygen. The amino group can be at the ortho, meta or para position, however, the m-aminobenzamidine is the strongest inhibitor. The ratio of acrylamide to monomer was found to affect the inhibition constant ($K_i$). A balance, therefore, must be made between the number of available binding sites (high m-aminobenzamidine content) and the strength of the binding force (corresponding to low $K_i$). The polymer having acrylamide-monomer ratio of 5:1 was chosen as a good compromise, however, ratios of 10:1 to 2:1 are also operable.

The concentration of the acrylamide used in the affinity ligand can also be varied. High acrylamide (polymer) concentrations provide a better binding efficiency, however, slow filtration rates are observed due to the increased viscosity of the polymer. Therefore, the optimum polymer concentration which represents the best compromise between these two effects was 0.75%, however, concentrations ranging from 0.3%–3% are also operable.

The bound trypsin is eluted from the affinity ligand using either L-arginine, benzamidine or m-aminobenzamidine. Although acidic solutions are often used to dissociate the m-aminobenzamidine-enzyme complex, unexpectedly they could not elute the bound trypsin effectively.

This affinity ligand has been used to purify trypsin in a batch and continuous process. Furthermore, trypsin can be adsorbed by the affinity polymer and stored until the enzyme is required for use or further processing. The purification procedures described are performed at 4° C. However, it is shown in Example 2 that the stability of trypsin absorbed to the affinity polymer was almost unchanged during two weeks of storage at either 4° C. or 25° C. Based on these results, the purification procedures can be performed at 4° C.–25° C.

In this invention, it has been demonstrated that a 98% pure product (trypsin) can be obtained in a high yield (90%) by an essentially one-step procedure using the affinity ultrafiltration technique. The method was proved to be very specific for trypsin while chymotrypsin was removed in the filtrate. Unlike many classical purification procedures where processes are generally oriented toward the recovery of a specific product, the method developed in this invention is fairly general and requires only the knowledge of a good ligand for the desired product. The binding of the ligand to the protein occurs in a homogeneous phase and it is likely more rapid and effective than in a heterogeneous phase (conventional affinity chromatography). As well, the synthesis of the water soluble affinity polymer requires no spacers which are currently used in the classical affinity chromatography. Ultrafiltration affinity purification is a gentle and efficient method that can be applied to large volumes. Such a unit operation has been well established and does not require any special installations and/or scale-up procedures. While no serious attempts have been made to utilize affinity purification in a continuous fashion, ultrafiltration affinity purification can be operated continuously on a large scale by constantly recirculating the ligand to the feed reservoir and therefore would offer a definite advantage.

EXAMPLES

The following specific examples are intended to illustrate more fully the nature of the present invention without acting as a limitation upon its scope.

EXAMPLE 1

Synthesis and Characterization of a Polymer for Trypsin Purification

Preparation of the polymer

N-acryloyl-m-aminobenzamidine (hereafter referred to as the monomer) was prepared from acryloyl chloride and m-aminobenzamidine. The reaction was conducted at 0° C. by adding 20 mL acryloyl chloride dropwise to 1 L aqueous solution containing 10 g m-aminobenzamidine in the presence of an excess quantity of sodium acetate (170 g). The addition of acryloyl chloride was completed within 10 minutes and the reaction was allowed to proceed for another 30 minutes. The reaction product was then precipitated by adjusting the pH to 4 with concentrated nitric acid. After dissolution in hot water, the product was recrystallized by adding dilute nitric acid (yield =55%).

The polymer was obtained by adding the monomer (0.33 g to 10 g and dissolved in 10 mL dimethyl sulfoxide) to 350 mL aqueous solution containing 10 g acrylamide. After adding 30 μL of N,N,N',N'-tetramethylethylenediamine and extensive flushing of the solution with nitrogen gas to remove oxygen, the polymerization was initiated by adding 40 mL of ammonium persulfate solution (concentration of 5 g/L). After two hours, the resulting solution was diluted 4-fold and passed through the Minitan Millipore ™ ultrafiltration system having 100,000 cut-off molecular weight membrane plates. By monitoring the absorbance of the filtrate in the range of 190–390 nm, it was observed that more than 80% of the polymer had molecular weight greater than 100,000. Measurement of the absorption at 280 nm also indicated that about 90% of the monomer was incorporated into the high molecular weight polymeric chains. Only the retentate was used for trypsin purification studies.

Effect of acrlyamide:monomer ratio on Inhibition Constant

As indicated by several researchers (B. F. Erlanger, N. Kokowsky and W. Cohen, Archives Biochem. and Biophys., 95, 271–278, 1961; and G. W. Schwert and Y. Takenaka, Biochim. Biophys. Acta, 16, 570–576, 1955), the trypsin inhibition kinetics of m-aminobenzamidine (m-AB) with respect to the substrate No-benzoyl-L-arginine p-nitroanilide is of a competitive manner. In this invention, it was further observed that the polymer containing m-AB exhibited the same mechanism of trypsin inhibition (data not shown). The inhibition constant, $K_i$, was determined to be 0.60±0.05 mM (expressed in monomer molarity) for polymers containing a small percentage of m-AB (i.e. acrylamide-monomer ratio greater than 10:1). However, $K_i$ increased significantly (greater than 1 mM) when the polymer contained high percentage of m-AB (i.e. acrylamide-monomer ratio smaller than 2:1). A balance, hence, must be made between the number of available binding sites (high m-AB content) and the strength of the binding force (corresponding to low $K_i$). The polymer having acrylamide-monomer ratio of 5:1 apparently offered a good compromise, it was therefore chosen for further studies.

Effect of acrylamide:monomer ratio on Trypsin Binding

In all experiments, the acrylamide concentration was 0.75% and the amount of trypsin and chymotrypsin was 750 mg each. As shown in Table I, the percentage of trypsin retained which was only 40% for high acrylamidemonomer ratio, increased to 90% when the ratio was 5:1. Experiments were also performed to ascertain that polymer containing no ligand did not retain trypsin, a proof of absence of non-specific binding. Table I also shows

TABLE I

| BINDING EFFICIENCY OF TRYPSIN TO POLYMERS AT 0.75% | | | | | |
|---|---|---|---|---|---|
| Acrylamide-monomer Ratio | m-AB (mg) | Trypsin Retained (mg) | % Trypsin Retained | Binding Ratio | Ratio Introduced |
| ∞ | 0 | 0 | 0 | — | — |
| 200:1 | 2.35 | 307 | 41 | 130 | 319 |
| 100:1 | 4.7 | 300 | 40 | 64 | 160 |
| 50:1 | 9.4 | 474 | 63 | 50 | 80 |
| 20:1 | 23.5 | 568 | 76 | 24 | 32 |
| 10:1 | 47 | 597 | 80 | 12.7 | 16 |
| 5:1 | 94 | 676 | 90 | 7.2 | 8 |

Volume of polymer solution: 75 mL
Weight of trypsin and chymotrypsin introduced: 750 mg each values of the binding ratio which is defined as the weight of retained trypsin divided by the amount of m-aminobenzamidine (m-AB) used in preparing the polymer. This ratio increased from 7.2 to 128 when less and less m-AB was present. In theory, the highest binding ratio should be around 120 since the molecular weights of trypsin and m-AB are about 25,000 and 210, respectively. For affinity polymers with high content of m-AB, it is almost impossible to attain such a theoretical ratio. Considering the 5:1 polymer, at 0.75% polymer concentration, the m-AB content in 75 mL solution is 94 mg. The corresponding equimolar weight of trypsin (11.2 g) simply cannot be dissolved in 75 mL of solution. However, with a polymer having a very low content of m-AB (e.g. polymer 200:1) the experimental data indicated that the theoretical binding ratio was actually achieved (Table I). As well, an excess of added trypsin did not necessarily produce a binding ratio approaching the theoretical value (e.g. polymer 100:1 in Table I and polymer 10:1 in Table II). The experimental results thus provide some insights to the binding retention process. Instead of being instant, solely governed by the amount of m-AB present, the binding process appears to be dynamic, whereas trypsin continually being attached to the ligand and being removed by the shear force.

Effect of acrylamide concentration on Trypsin binding

Following the addition of 250 mL of polymer

TABLE II

BINDING EFFICIENCY OF TRYPSIN TO POLYMERS AT 0.15%

| Acrylamide-monomer Ratio | m-AB (mg) | Trypsin Retained (mg) | % Trypsin Retained | Binding Ratio | Ratio Introduced |
|---|---|---|---|---|---|
| 20:1 | 4.7 | 540 | 45 | 115 | 255 |
| 10:1 | 9.4 | 658 | 55 | 70 | 128 |
| 5:1 | 18.8 | 782 | 65 | 41.5 | 64 |

Volume of polymer solution: 75 mL
Weight of trypsin and chymotrypsin introduced: 1200 mg each 5:1 to a mixture of trypsin and chymotrypsin (2.5 g of each enzyme, in 50 mL of Tris buffer containing 10 mM $CaCl_2$), the solution was incubated for two hours and then ultrafiltered by using the 100,000 MW cut-off Millipore TM membrane plates. Buffer was added to the system at the same rate as that of filtration (1 L/hr) in order to maintain a constant system volume throughout the operation. After three hours of the experiment, the activity of chymotrypsin detected in the retentate and the filtrate was 2% and 95%, respectively. Meanwhile, the retentate contained about 90% of trypsin activity, the remaining 10% was in the filtrate. It is, therefore, evident that the polymer possesses specific affinity toward trypsin.

The binding efficiency between the affinity polymer and trypsin is dependent upon the concentration of the polymer solution. At 0.75% (weight per volume) polymer concentration, the percentage of trypsin retained was about 90%. This level decreased to 54% when the concentration was reduced to 0.03% eventhough the amount of enzyme introduced was also reduced by the same factor (0.75/0.03=25). This behaviour could be explained by the fact that decreasing the acrylamide concentration makes the trypsin bound to the ligand more susceptible to the shear force resulting from the high flow rates through the membrane systems. It was, however, noted that the elution profile for chymotrypsin in the retentate and filtrate was independent of the acrylamide concentration used. Since high polymer concentrations provide a better binding efficiency, it would be desirable to work with concentrated polymer solutions. However, high polymer concentrations always result in a very slow filtration rate due to the increasing viscosity. Therefore, there is an optimal polymer concentration which represents the best compromise between these two effects. With the present system, the concentration of 0.75% appeared to provide the best compromise, it was therefore used in all subsequent experiments. In accordance with the results presented so far, the polymer 5:1 at 0.75% clearly represents the best binding efficiency (676 mg of trypsin retained by 560 mg polymer). It was, therefore, used exclusively in subsequent experiments.

Elution characteristics

Figure 1:
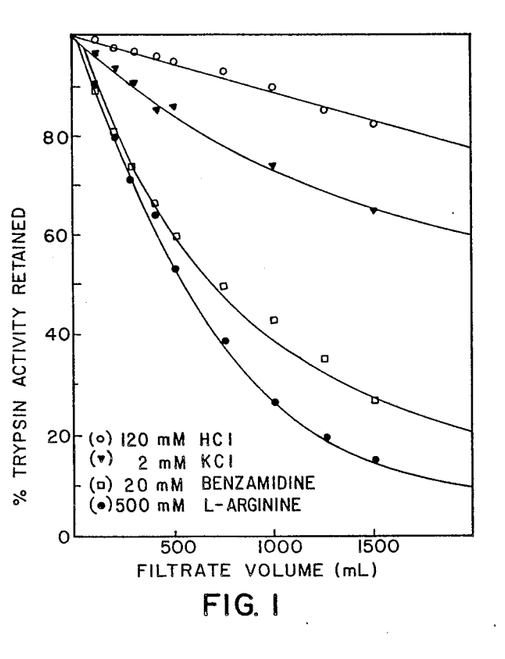
FIG. 1 illustrates the eluting characteristics of different agents as represented by trypsin activity of the retentate.

Investigation was next conducted on the eluting characteristics of four agents (FIG. 1). A polymer solution (polymer 5:1 at 0.75%) containing 300 mg trypsin was ultrafiltered while an eluting solution was added at the same rate as the filtrate stream. In all cases, the released enzyme was fully recovered in the filtrate. It is obvious that arginine was the most effective eluting agent. Although acidic solution is often used to dissociate the m-AB-enzyme complex (J. J. Bechet and A. D'albis, Biochim. Biophys. Acta, 178, 561–576, 1969; and M. Schneider, C. Guillot and B. Lamy, Annals of N.Y. Academy of Sciences, 369, 257–263, 1981), unexpectedly, it could not elute the bound trypsin efficiently. Such behaviour could be due to an interference to the membrane performance at this operating condition. The interference was also observed when alkaline conditions were used. This observation thus indicated that it is importtant to maintain a neutral pH when using the affinity polymer in conjunction with the ultrafiltration membrane plates. It should be noted that chymotrypsin, as well as trypsin, in a polymer solution at low pH passed through the ultrafilter very slowly. Therefore, even if trypsin were released from the polymer at low pH, it would not pass through the ultrafiltration membrane. The cause of the inability of the membrane to perform, in the presence of the polymer, at basic or acidic conditions remains to be investigated. Arginine could be chosen as the best eluant since it is much less expensive than benzamidine. Arginine has been experimentally determined to be a competitive inhibitor ($K_i = 41 \pm 3$ mM, data not shown) with respect to the substrate $N^\alpha$-benzoyl-L-arginine p-nitroanilide for trypsin. The data also shows that the efficiency of elution of trypsin from the polymer increases with the arginine concentration. The three concentrations tested were 150 mM, 500 mM, and 1.5M. However, the optimal elution condition appeared to be 500 mM of arginine, since at 1.5M arginine this solution is too viscous and thus results in a very low filtration rate.

Tests were also performed to determine whether the elution of trypsin with arginine was affected by the acrylamide:monomer ratio and the polymer concentration. The trypsin bound to polymers having low m-AB content (i.e. polymer 30:1 and 0.75% acrylamide and polymer 5:1 and acrylamide concentration 0.15%) can be eluted easily. However, the binding capacity of these polymers is not very high. Consequently, a choice must be made concerning the m-AB content (e.g. the acrylamide-monomer ratio) so that a large amount of trypsin can be bound and eluted easily. The results obtained in this work lead to the conclusion that the polymer 5:1, with an acrylamide concentration of 0.75%, possesses optimal characteristics. As well, for the same polymer, the elution rate is faster if the solution concentration is reduced.

Stability and reusability of the polymer

The stability and reusability of the polymer has also been investigated. After six months of storage at 4° C., solutions of polymer were filtered through the 100,000 MW ultrafiltration system and the measurement of the optical density confirmed that the polymers had neither degraded into smaller fragments nor had they lost ligand molecules. It was also observed that the same percentage of trypsin could be bound to the polymers stored for six months as compared to the freshly synthesized polymer. The same polymer solution could be re-used for more than one cycle of binding and elution (Table III). This is an important aspect because it indicated that the polymer can be regenerated and employed on a continuous purification system.

EXAMPLE 2

Use of Affinity Polymer for Trypsin Storage and Stability

Trypsin can be adsorbed by the affinity polymer and stored until this enzyme is required for use or further processing. Such an applicability was demonstrated in this application by monitoring the trypsin activity in a trypsin-polymer solution (5 mg trypsin/mL in 25 mM Tris pH 8). The trypsin activity remained almost unchanged during two weeks of storage at either 4° C. or 25° C. Without the affinity polymer, the trypsin retained only half of its activity at 25° C. after three days even though this solution was stabilized by adding an appropriate amount of calcium. It was further shown that at 4° C. without the affinity polymer trypsin retained approximately 70% of its original activity after 10 days.

The binding efficiency of this polymer can also be used to remove trypsin from a proteolytic digestion mixture to halt the reaction. Because of the tendency of trypsin to undergo autodigestion during purification and storage, it is always desirable to develop a rapid and simple method for purification of such an enzyme. Therefore, this polymer can also be used to stabilize trypsin.

EXAMPLE 3

Use of Affinity Polymer to Purify Trypsin from a Mixture of Trypsin and Chymotrypsin Further work on this affinity polymer was pursued for recovering the enzyme trypsin from a mixture of trypsin and chymotrypsin. Following the addition of 250 mL of polymer (5:1 acrylamide/monomer ratio) to a mixture of trypsin and chymotrypsin (2.5 g of each enzyme, in 50 mL of 25 mM Tris buffer pH 8.2 containing 10 mM $CaCl_2$), the solution was incubated for two hours at 4° C. The resulting solution was ultrafiltered by using the 100,000 MW cut-off Millipore TM plates. During this experiment, the retentate volume was kept constant by adding the buffer, thus resulting in a constant filtration rate (1 L/hr) throughout the purification. The molecular weight of chymotrypsin is 25,300, i.e. if this enzyme is not bound to the polymer, it will pass through the membranes.

Figure 2:
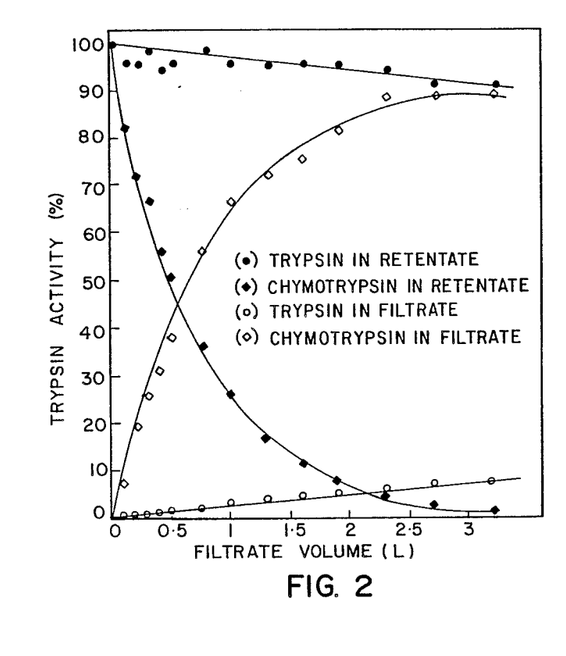
FIG. 2 shows typical results of a batch affinity-ultrafiltration purification of trypsin from a mixture of trypsin and chymotrypsin.

After three hours of the experiment, the activity of chymotrypsin remaining in the retentate was less than 2% indicating that the non-specific binding of the synthesized affinity polymer was very minimal. On the other hand, the chymotrypsin activity recovered in the filtrate of 3000 mL was greater than 90% (FIG. 2). The retentate contained about 90% of the trypsin activity while the remaining 10% of this enzyme was detected in the filtrate. As usual, one has to compromise between the yield desired and the degree of purity obtained. As shown in FIG. 2, the yield of trypsin recovered (90%) corresponding to only 2% (or less) chymotrypsin contaminant in the product. However, when a higher level of contamination was tolerable the process yield could be significantly higher (95% yield versus 10% chymotrypsin contaminant). This study also verified that the bound trypsin could be eluted easily by using any of the following solutions: 500 mM arginine with 10 mM $Ca^{++}$ (for prevention of autodigestion) in Tris buffer pH 8; 2M KCl with 10 mM $Ca^{++}$ in pH 8 Tris or 10 mM m-aminobenzamidine (data not shown).

EXAMPLE 4

Development of a Continuous Affinity-Ultra-filtration Process

Figure 3:
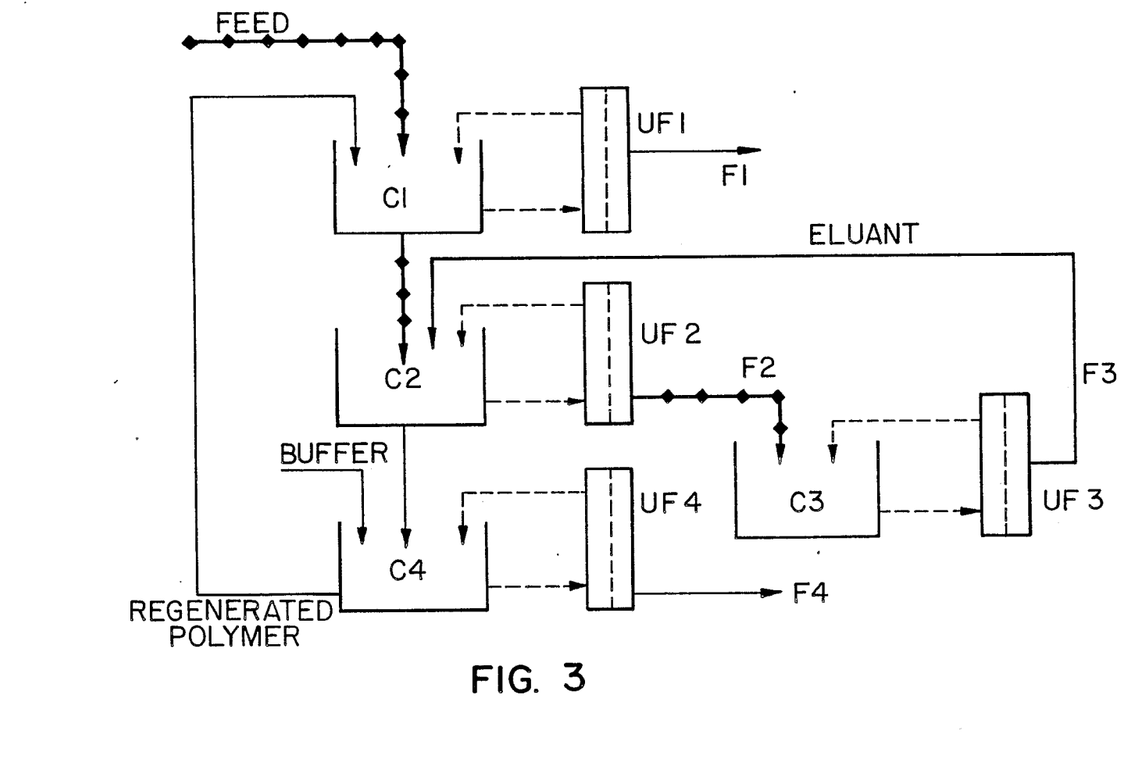
FIG. 3 depicts a flow diagram of the continuous affinity ultrafiltration process.

A schematic diagram for the continuous affinity ultrafiltration system is shown in FIG. 3. Enzyme solution (in 50 mM Tris pH 8, 10 mM $Ca^{++}$) containing 100 mg/L each of trypsin and chymotrypsin was peristaltically pumped at a flow rate of 25 mL/min to a container (C1), containing 100 mL of the affinity polymer (0.75% solution). The feed rate of each of trypsin and chymotrypsin therefore is 150 mg/hr. The resulting solution was ultrafiltered through UF1. Pressure was adjusted to set a filtration rate of 25 mL/min resulting in a constant volume in C1. Trypsin was retained (in C1), since it bound to the macromolecular affinity polymer, while unbound chymotrypsin passed through the membranes into the filtrate stream F1. After 2.5 hours fresh polymer (0.75% by weight) was added, concurrently with the enzyme solution, at 0.66 mL/min, to C1 while its content was transferred to C2 at the same rate. After another 2.5 hours, the volume accumulated in C2 attained 100 mL, containing mainly the isolated affinity polymer-trypsin complex. At this point, 24 g of L-arginine-HCl was added to C2 (yielded 1M arginine solution) and the resulting solution was ultrafiltered by UF2

TABLE III

| CONSECUTIVE BINDING - ELUTION WITH SAME POLYMER SOLUTION | | | | | | |
|---|---|---|---|---|---|---|
| | % Enzyme Activity | | | | | |
| | Binding | | | | Elution | |
| Cycle | Trypsin | | Chymotrypsin | | Trypsin | |
| Number | Retentate | Filtrate | Retentate | Filtrate | Retentate | Filtrate |
| 1 | 88 | 12 | 3 | 97 | 2 | 86 |
| 2 | 90 | 10 | 2 | 98 | 6 | 84 |
| 3 | 87 | 13 | 3 | 97 | 3 | 84 |

1500 mg each of trypsin and chymotrypsin introduced at the beginning of each cycle.
Eluting solution: 1 M Arginine
Filtrate volume in each step: 2.5 L with a filtration rate of 25 mL/min. Trypsin was dissociated from the affinity polymer and then passed to the filtrate F2 which was collected in C3 (containing 200 mL of 1M L-arginine-HCl in Tris buffer at the beginning). The solution in C3 was processed by UF3, the filtration rate of which was adjusted to 25 mL/min, leaving the volume in C3 constant with trypsin accumulated therein. The filtrate stream F3, containing most of the arginine was recycled to C2, effectively leaving the volume in C2 constant. The retentate of UF2 (remained in C2), mostly made up of affinity polymer in 1M L-arginine-HCl, was transferred at a rate of 0.66 mL/min to C4 containing 100 mL of a fresh affinity polymer solution (0.75%). Buffer solution was continually added to C4 (about 30 mL/min) while its content was processed by UF4 at a filtrate rate of 30 mL/min leaving the volume of C4 constant. Arginine was removed (in F4) thereby leaving the affinity polymer (in C4) regenerated and ready to be recycled to C1. In order to maintain an arginine concentration of 1M in the second ultrafiltration system, 35 mL of 2M L-arginine-HCl solution was added to C2 every hour while 35 mL of F3 was withdrawn and discarded. Samples from all four containers were withdrawn periodically, the enzyme activities were assayed, and the content of each enzyme in each container was calculated.

In the experiments using the crude preparation, the operation was similar with the following particulars: the crude concentration in the feed was 375 mg/L, total start up time was 10 hours, and the eluant was 50 mM benzamidine.

All experiments were performed at 4° C. All ultrafiltration units were Millipore Minitan TM, each was equipped with four membrane plates, each of which had a 60 cm$^2$ filtration area. The molecular weight cut-off of UF3 was 10,000, other units had molecular weight cut-offs of 100,000.

In Example 3, the mixture of trypsin and chymotrypsin was incubated with the affinity polymer for two hours before filtration Similar results to those obtained in Example 3 were also achieved if an enzyme solution was added to the polymer and the resulting solution was ultrafiltered immediately. This is an important finding since it implies that one could add the enzyme solution directly to the polymer solution which is being passed through the ultrafiltration unit, instead of having to set up a holding tank for the binding to take place in, prior to running.

Another experiment was conducted to evaluate the system's efficiency to pass chymotrypsin in the presence of trypsin and the polymer. When the filtration rate was increased three-fold (from 9 to 27 mL/min), the same volume ratio still resulted in the same percentage of removal (data not shown). Such a finding thus indicates that it is possible to operate at the highest filtration rate (afforded by the system), without sacrificing its effectiveness in passing chymotrypsin. Therefore, a filtration rate of 25 mL/min was used to obtain the results presented hereafter.

Figure 4:
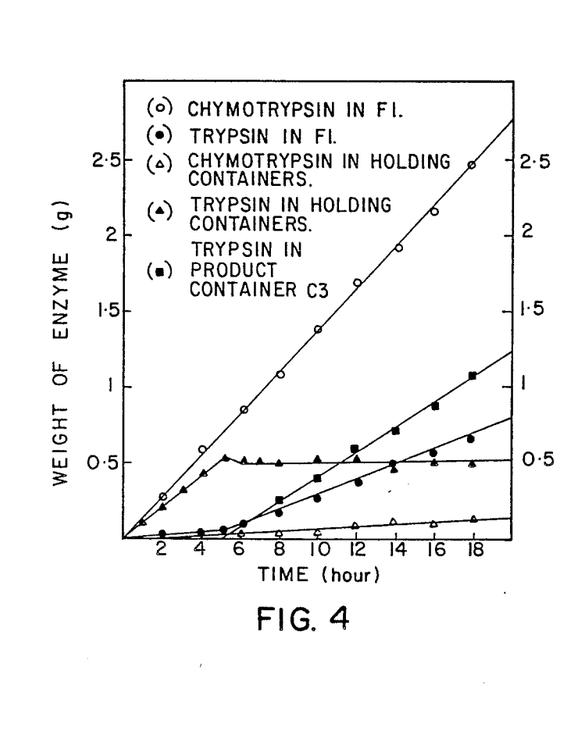
FIG. 4 shows the performance of the continuous system fed with a trypsin-chymtrypsin mixture. Accumulative enzyme concentrations are present.

A series of continuous affinity ultrafiltration experiments was then conducted, a typical set of results is presented in FIG. 4. In general, at any time nearly 100% of the introduced chymotrypsin was collected in the filtrate while 4% was detected in the holding containers. About 30% of the starting trypsin was lost in F1 with 60% of the activity being recovered in the four retentates. It should be noted that the enzyme activities (of trypsin and chymotrypsin) detected in the system (by adding activities in various containers) usually do not add up to the input activity due to experimental errors.

As shown in FIG. 4, after the start up period, the system quickly attained a steady-state as reflected by a constant amount of trypsin in the holding containers. As well, the rate of trypsin accumulation in C3 (product container) was almost constant (around 80 mg/hr) while the weight of chymotrypsin always amounted to 9% that of trypsin. In brief, the continuous process can accomplish a yield of 53.3% at 91% product purity.

Figure 5:
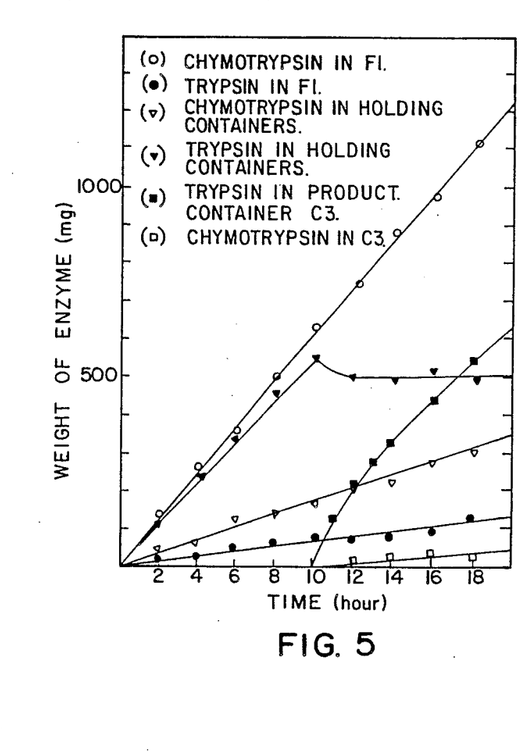
FIG. 5 depicts the performance of the continuous system fed with a solution of crude preparation from pig pancreas.

The effectiveness of the process was further investigated by using the crude preparation from pig pancreas. This preparation contained 12% trypsin, by weight, and a similar amount chymotrypsin. With a feed rate of 25 mL/min, at a concentration of 375 mg of crude per liter, the feed rate of trypsin, or chymotrypsin, therefore, is equal to 67.5 mg/hr. At the end of the start up period (10 hours), a high level of chymotrypsin was detected in C1. This could be due to the fact that the crude preparation contained many other unknown proteins which could bind to the affinity polymer together with trypsin. Such a complex could, in turn, interact with the contaminating chymotrypsin and thus reduce the specificity of the system. Another possibility could be the interaction between chymotrypsin and impurities, thus increasing the apparent molecular weight of chymotrypsin. However, the high level of chymotrypsin in C1 indicated the need for a specific elution procedure. Recourse was therefore attempted through the use of benzamidine, in expectation that only trypsin would be released by this specific inhibitor. This expectation was indeed confirmed by the results presented in FIG. 5. At the end of the start-up period, 550 mg of trypsin was detected in C1, contaminated with 170 mg of chymotrypsin (23.6% contamination). However, after 10 hours of continuous operation, using benzamidine as eluant, the product container C3 exhibited trypsin activity equal to 630 mg contaminated with only 20 mg of chymotrypsin (3% contamination). Based on the last 5 hours of operation, when the rate of trypsin accumulation in C3 was 52 mg/hr, the yield is 77%, at 97% purity.

We claim:
1. An affinity-ultrafiltration method for purifying trypsin comprising:
   (a) incubating an enzyme containing aqueous mixture, containing trypsin, with a water-soluble affinity polymer having specificity for trypsin, formed by copolymerizing N-acryloyl-aminobenzamidine and acrylamide to an average molecular weight of at least about 100,000, to form a soluble polymer-trypsin complex;
   (b) ultrafiltrating the mixture of (a) to remove all enzymes not bound to the affinity polymer, and retaining the enzyme-affinity polymer complex;
   (c) removing the trypsin, from the enzyme-affinity polymer complex, by eluting with an eluting solution selected to dissociate the complex without inhibiting ultrafiltration, and recovering the released affinity polymer; and
   (d) ultrafiltering the resulting solution from (c) to separate the purified trypsin and the eluent.
2. The method of claim 1 wherein the incubation of step (a) occurs for a period of up to 2 hours at 4° C.–25° C.

3. The method of claim 1 wherein the incubation of step (a) occurs for a period of up to 2 hours at about 4° C.

4. The method of claim 1 wherein the eluting solution of step (c) contains a compound selected from the group consisting of benzamidine, L-arginine, potassium chloride and aminobenzamidine.

5. The method of claim 4 wherein the eluting solution is 150 mM to 1.5M L-arginine in Tris buffer, pH about 8, with about 10 mM $Ca^{++}$.

6. The method of claim 5 wherein the eluting solution is about 500 mM L-arginine in Tris buffer, pH about 8, with about 10 mM $Ca^{++}$.

7. The method of claim 1 wherein the mole ratio of acrylamide to affinity monomer is within the range 2:1 to 10:1.

8. The method of claim 1 wherein during copolymerization the concentration of acrylamide is 0.3–3.0%.

9. The method of claim 1 wherein the mole ratio of acrylamide to affinity monomer is about 5:1 and the concentration of acrylamide during copolymerization is about 0.75%.

10. The method of claim 1 wherein the ultrafiltration of step (b) is performed using filters with a molecular weight cut-off of about 100,000 and the ultrafiltration of step (d) is performed using filters with a molecular weight cut-off of about 10,000.

11. The method of claim 1 wherein the affinity monomer is N-acryloyl-m-aminobenzamidine.

12. A continuous affinity-ultrafiltration process for purifying trypsin comprising:
  (a) contacting an aqueous enzyme solution, containing trypsin, with water-soluble affinity polymer having specificity for trypsin, formed by copolymerizing N-acryloyl-aminobenzamidine and acrylamide to an average molecular weight of at least about 100,000 to form a soluble polymer-trypsin complex;
  (b) ultrafiltering the solution of (a) to remove all enzymes not bound to the affinity polymer and to recover the affinity polymer-trypsin complex;
  (c) adding fresh affinity polymer and enzyme solution to replace that withdrawn in step b;
  (d) adding an eluting solution to the withdrawn complex from step (b) selected to dissociate the trypsin from the affinity polymer without inhibiting ultrafiltration;
  (e) ultrafiltering the solution from step (d) to separate the dissociated trypsin and eluent solution rom the affinity polymer;
  (f) ultrafiltering the residual solution from step (e) to recover the purified trypsin; and
  (g) repeating steps (b)–(f).

13. The method of claim 12 wherein the ultrafiltration of steps (b) and (e) are performed using filters with a molecular weight cut-off of about 100,000 and the ultrafiltration of step (f) is performed using filters with a molecular weight cut-off of about 10,000.

14. The method of claim 12 wherein the eluting solution of step (d) contains a compound selected from the group consisting of L-arginine and benzamidine.

15. The method of claim 14 wherein the eluting solution contains one of about 1M L-arginine and about 50 mM benzamidine.

16. The method of claim 12 wherein the eluting solution is recovered from step (f) and recirculated to step (d).

17. The method of claim 12 wherein the affinity polymer from step (d) is regenerated and recycled for re-use in step (a).

18. The method of claim 12 wherein the affinity-ultrafiltration process is performed at about 4° C.

19. The method of claim 12 wherein the affinity polymer in step (a) is formed by copolymerizing N-acryloyl-m-aminobenzamidine and acrylamide.

20. The method of claim 12 wherein the mole ratio of acrylamide to affinity monomer is within the range 2:1 to 10:1.

21. The method of claim 12 wherein during copolymerization the concentration of acrylamide is 0.3–3.0%.

22. The method of claim 12 wherein the mole ratio of acrylamide to affinity monomer is about 5:1 and the concentration of acrylamide during copolymerization is about 0.75%.

23. A method of stabilizing and storing trypsin comprising binding trypsin to the affinity polymer of claim 1 step (a) and storing the trypsin-polymer complex for a time up to the order of about two weeks.

24. The method of claim 23 wherein after storage the trypsin is recovered by elution with a reagent selected to dissociate trypsin from the complex without inhibiting ultrafiltration, and ultrafiltration.

* * * * *